(12) United States Patent
Wogoman et al.

(10) Patent No.: US 11,141,291 B2
(45) Date of Patent: Oct. 12, 2021

(54) FEMORAL TRIAL COMPONENTS AND ASSOCIATED ORTHOPAEDIC SURGICAL METHOD OF USE

(71) Applicant: DePuy Ireland Unlimited Company, Ringaskiddy (IE)

(72) Inventors: Thomas E. Wogoman, Warsaw, IN (US); Travis D. Bennett, Huntington, IN (US); Kevin J. Zylka, Fort Wayne, IN (US); Amitkumar Madhukar Mane, South Whitley, IN (US); Mark A. Heldreth, Warsaw, IN (US)

(73) Assignee: DEPUY IRELAND UNLIMITED COMPANY

( * ) Notice: Subject to any disclaimer, the term of this patent is extended or adjusted under 35 U.S.C. 154(b) by 131 days.

(21) Appl. No.: 16/458,077

(22) Filed: Jun. 30, 2019

(65) Prior Publication Data
US 2020/0405506 A1  Dec. 31, 2020

(51) Int. Cl.
| | |
|---|---|
| *A61F 2/46* | (2006.01) |
| *A61B 17/17* | (2006.01) |
| *A61F 2/38* | (2006.01) |
| *A61B 17/15* | (2006.01) |

(52) U.S. Cl.
CPC ........ *A61F 2/4684* (2013.01); *A61B 17/1764* (2013.01); *A61F 2/3859* (2013.01); *A61B 17/155* (2013.01); *A61F 2/389* (2013.01); *A61F 2/3836* (2013.01)

(58) Field of Classification Search
CPC . A61B 17/154; A61B 17/155; A61B 17/1764; A61F 2002/30616; A61F 2/3859; A61F 2/3886; A61F 2/389; A61F 2/4684; A61F 2/3836
See application file for complete search history.

(56) References Cited

U.S. PATENT DOCUMENTS

| | | | | |
|---|---|---|---|---|
| 4,209,861 A * | 7/1980 | Walker | ................ | A61F 2/3886 623/20.27 |
| 6,926,738 B2 * | 8/2005 | Wyss | ................... | A61F 2/3868 623/18.11 |
| 8,403,994 B2 * | 3/2013 | Maloney | .............. | A61F 2/3859 623/20.35 |
| 8,480,752 B2 * | 7/2013 | Dun | ...................... | A61F 2/3886 623/20.33 |
| 9,011,453 B2 * | 4/2015 | Parisi | ................... | A61F 2/3859 606/88 |
| 2012/0078263 A1 | 3/2012 | Parisi et al. | | |
| 2014/0058398 A1 | 2/2014 | Kaneyama et al. | | |

(Continued)

OTHER PUBLICATIONS

Extended European search report for Application No. 20178171.3-1122, dated Nov. 25, 2020, 8 pages.

*Primary Examiner* — Zade Coley

(74) *Attorney, Agent, or Firm* — Barnes & Thornburg LLP

(57) ABSTRACT

An orthopaedic surgical system for a total knee implant includes a plurality of commonly-sized femoral trial components. Each commonly-sized femoral trial component includes a first femoral condyle having a first articulation surface configured to engage a tibial component, and a second femoral condyle may be spaced apart from the first femoral condyle. The second femoral condyle has a second articulation surface configured to engage the tibial component. An anterior cam is positioned between the first femoral condyle and the second femoral condyle. A method of using such a system is also disclosed.

18 Claims, 10 Drawing Sheets

(56) References Cited

U.S. PATENT DOCUMENTS

2014/0114319 A1     4/2014   Wilkinson
2019/0029830 A1     1/2019   Nguyen et al.

\* cited by examiner

FEMORAL TRIAL COMPONENTS AND ASSOCIATED ORTHOPAEDIC SURGICAL METHOD OF USE

TECHNICAL FIELD

The present disclosure relates to orthopaedic knee prosthetic systems and, more specifically, to orthopaedic knee prosthetic systems including anterior stabilized orthopaedic knee prosthetics for use in total knee arthroplasty procedures.

BACKGROUND

Total knee replacement (TKR), also referred to as total knee arthroplasty (TKA), is a surgical procedure where worn, diseased, or damaged surfaces of a knee joint are removed and replaced with artificial surfaces. An orthopaedic knee implant generally has three components a distal femoral component, a proximal tibial component, and a bearing component positioned therebetween.

SUMMARY

According to one aspect of the disclosure, an orthopaedic surgical system for a total knee implant may include a plurality of commonly-sized femoral trial components. Each commonly-sized femoral trial component may include a first femoral condyle having a first articulation surface configured to engage a tibial component. A first bone-facing surface may be positioned opposite the first articulation surface and may be configured to engage a distal end of a patient's femur. A second femoral condyle may be spaced apart from the first femoral condyle. The second femoral condyle may have a second articulation surface configured to engage the tibial component. A second bone-facing surface may be positioned opposite the second articulation surface and may be configured to engage the distal end of the patient's femur. An anterior cam may be positioned between the first femoral condyle and the second femoral condyle. The anterior cam may be configured to engage an anterior surface of the tibial component. A peg may extend away from the first bone-facing surface. An anterior-posterior distance may be defined between the peg and the anterior cam. Each commonly-sized femoral trial component of the plurality of commonly-sized femoral trial components may have an anterior-posterior distance that is different than the anterior-posterior distance of every other commonly-sized femoral trial component included in the plurality of commonly-sized femoral trial components.

In some embodiments, the anterior cam may include a posterior surface configured to engage the anterior surface of the tibial component. The peg may be positioned posteriorly of the anterior cam. Each commonly-sized femoral trial component of the plurality of commonly-sized femoral trial components further may include a second peg extending away from the second bone-facing surface. The first and second pegs may be positioned an equal distance away from the anterior cam in the anterior-posterior direction.

In some embodiments, the plurality of commonly-sized femoral trial components may include a first femoral trial component and a second femoral trial component. The second femoral trial component may have an anterior-posterior distance that is about 1.5 millimeters less than the anterior-posterior distance of the first femoral trial component. The plurality of commonly-sized femoral trial components may include a third femoral trial component having an anterior-posterior distance that is about 1.5 millimeters greater than the anterior-posterior distance of the first femoral trial component.

According to another aspect of the disclosure, an orthopaedic surgical system may include a tibial component including a first bearing surface. A second bearing surface may be spaced apart from the first bearing surface. A post may be positioned between the first and second bearing surfaces. A plurality of commonly-sized femoral trial components may be configured to articulate relative to the tibial component between a full extension position and a full flexion position. Each commonly-sized femoral trial component of the plurality of commonly-sized femoral trial components may include a first femoral condyle having a first articulation surface sized and shaped to articulate on the first bearing surface of the tibial component and a first bone-facing surface positioned opposite the first articulation surface and configured to engage a distal end of a patient's femur. A second femoral condyle may be spaced apart from the first femoral condyle. The second femoral condyle may have a second articulation surface sized and shaped to articulate on the second bearing surface of the tibial component and a second bone-facing surface positioned opposite the second articulation surface and configured to engage the distal end of the patient's femur. An anterior cam may be positioned between the first femoral condyle and the second femoral condyle. The anterior cam may have a posterior surface configured to engage an anterior surface of the post of the tibial component. A peg may be positioned posteriorly of the anterior cam, may extend away from the first bone-facing surface, and may be configured to engage the distal end of the patient's femur to fix the femoral trial component relative to the patient's femur. An anterior-posterior distance may be defined between the peg and the anterior cam. Each commonly-sized femoral trial component of the plurality of commonly-sized femoral trial components may have an anterior-posterior distance that is different than the anterior-posterior distance of every other commonly-sized femoral trial component included in the plurality of commonly-sized femoral trial components.

In some embodiments, the posterior surface of the anterior cam of each commonly sized femoral trial component may be engaged with the anterior surface of the post when the femoral trial component and the tibial component are in the full extension position. The first femoral trial component may be configured to locate patient's femur in a first trialing position relative to the patient's tibia when the tibial component is secured to a tibia of the patient, the first femoral trial component is fixed relative to the patient's femur, and the first femoral trial component and the tibial component are in the full extension position. The plurality of femoral trial components may include a second femoral trial component having an anterior-posterior distance that is less than the anterior-posterior distance of the first femoral trial component. The second femoral trial component may be configured to locate the patient's femur in a second trialing position relative to the patient's tibia when the tibial component is secured to the patient's tibia, the second femoral trial component is fixed relative to the patient's femur, and the second femoral trial component and the tibial component are in the full extension position. The second trialing position of the patient's femur may be anterior of first trialing position. The plurality of femoral trial components may include a third femoral trial component having an anterior-posterior distance that is greater than the anterior-posterior distance of the first femoral trial component. The third femoral trial component may be configured to locate the patient's femur in a third trialing position relative to the patient's tibia when the tibial component is secured to the patient's tibia, the third femoral trial component is fixed relative to the patient's femur, and the third femoral trial component and the tibial component are in the full extension position. The third trialing position of the patient's femur may be posterior of the first trialing position. In some embodiments, the posterior surface of the anterior cam of each commonly-sized femoral trial component may disengage from the anterior surface of the post as the femoral trial component articulates relative to the tibial component toward the full flexion position.

In some embodiments, each commonly-sized femoral trial component may include a second peg extending away from the second bone facing surface. The first and second pegs may be spaced apart a first medial-lateral distance and may be positioned an equal distance away from the anterior cam in the anterior-posterior direction.

In some embodiments, a cutting block may include a bone-engaging surface. An outer surface may be positioned opposite the bone-engaging surface. A pair of guide bores may include a first and second guide bore each extending through the bone-engaging surface and the outer surface of the cutting block. The first and second guide bores may be spaced apart a second medial-lateral distance equal to the first medial-lateral distance. The cutting block may include a plurality of pairs of guide bores extending through the bone-engaging surface and the outer surface of the cutting block. Each pair of guide bores may include a first and second guide bore spaced apart the second medial-lateral distance.

According to yet another aspect of the disclosure, a method of using an orthopaedic surgical system may include securing a tibial component to a proximal end of a patient's tibia. The method may also include selecting a first femoral trial component including a first femoral condyle, a second femoral condyle spaced apart from the first femoral condyle, an anterior cam positioned between the first femoral condyle and the second femoral condyle, a first peg extending from the first femoral condyle, positioned posteriorly of the anterior cam, and spaced apart a first anterior-posterior distance from the anterior cam, and a second peg extending from the second femoral condyle, positioned posteriorly of the anterior cam, and spaced apart the first anterior-posterior distance from the anterior cam. The method may also include inserting the first and second pegs of the first femoral trial component into a pair of surgically prepared holes formed in the distal end of the patient's femur to fix the first femoral trial component relative to the patient's femur. The method may also include removing the first femoral trial component from the patient's femur. The method may also include selecting a second femoral trial component including a first femoral condyle, a second femoral condyle spaced apart from the first femoral condyle, an anterior cam positioned between the first femoral condyle and the second femoral condyle, a first peg extending from the first condyle, positioned posteriorly of the anterior cam, and spaced apart a second anterior-posterior distance from the anterior cam, and a second peg extending from the second femoral condyle, positioned posterior of the anterior cam, and spaced apart the second anterior-posterior distance from the anterior cam. The second anterior-posterior distance may be less than the first anterior-posterior distance. The method may also include inserting the first and second pegs of the second femoral trial component into the pair of surgically prepared holes formed in the distal end of the patient's femur to fix the second femoral trial component relative to the patient's femur.

In some embodiments, the method may include aligning a pair of guide bores of a femoral cutting block with a pair of fixation pins inserted into the surgically prepared holes formed in the distal end of the patient's femur. The femoral cutting block may have a bone-engaging surface and an outer surface positioned opposite the bone-engaging surface. The pair of guide bores may extend through the bone-engaging surface and the outer surface of the femoral cutting block. The method may also include advancing the femoral cutting block into engagement with the distal end of the patient's femur by advancing the guide bores of the femoral cutting block along the fixation pins.

In some embodiments, the method may include selecting a third femoral trial component including a first femoral condyle, a second femoral condyle spaced apart from the first femoral condyle, an anterior cam positioned between the first femoral condyle and the second femoral condyle, a first peg extending from the first femoral condyle, positioned posterior of the anterior cam, and spaced apart a third anterior-posterior distance from the anterior cam, and a second peg extending from the second femoral condyle, positioned posteriorly of the anterior cam, and spaced apart the third anterior-posterior distance from the anterior cam. The third anterior-posterior distance may be greater than the first anterior posterior distance. The method may also include inserting the first and second pegs of the third femoral trial component into the pair of surgically prepared holes formed in the distal end of the patient's femur to fix the third femoral trial component relative to the patient's femur.

In some embodiments, the method may include rotating the first femoral trial component relative to the tibial component into a full extension position to move the patient's femur into a first position relative to the patient's tibia. The method may also include rotating the second femoral trial component relative to the tibial component into the full extension position to move the patient's femur into a second position relative to the patient's tibia. The second position may be located anterior of the first position. The method may also include rotating the third femoral trial component relative to the tibial component into the full extension position to move the patient's femur into a third position relative to the patient's tibia. The third position may be located posterior of the first position.

According to a further aspect of the disclosure, an orthopaedic surgical system for a total knee implant may include a cutting block including a bone-engaging surface, an outer surface positioned opposite the bone-engaging surface, a first guide bore, and a second guide bore positioned anterior of the first guide bore such that a first anterior-posterior distance is defined between the first guide bore and the second guide bore. A plurality of commonly-sized femoral trial components may be provided. Each commonly-sized femoral trial component may include a first femoral condyle having a first articulation surface configured to engage a tibial component and a first bone-facing surface positioned opposite the first articulation surface and configured to engage a distal end of a patient's femur. A second femoral condyle may be spaced apart from the first femoral condyle. The second femoral condyle may have a second articulation surface configured to engage the tibial component. A second bone-facing surface may be positioned opposite the second articulation surface and configured to engage the distal end of the patient's femur. An anterior cam may be positioned between the first femoral condyle and the second femoral condyle. The anterior cam may be configured to engage an anterior surface of the tibial component. A peg may extend away from the first bone-facing surface. An anterior-posterior distance may be defined between the peg and the anterior cam of each commonly-sized femoral trial component of the plurality of commonly-sized femoral trial components. The plurality of commonly-sized femoral trial component may include a first commonly-sized femoral trial component and a second commonly-sized femoral trial component. A difference between the anterior-posterior distance of the first commonly-sized femoral trial component and the anterior-posterior distance of the second commonly-sized femoral trial component may be equal to the first anterior-posterior distance of the cutting block.

In some embodiments, the difference between the anterior-posterior distance of the first commonly-sized femoral trial component and the anterior-posterior distance of the second commonly-sized femoral trial component may be 1.5 millimeters. The first anterior-posterior distance of the cutting block may be 1.5 millimeters.

In some embodiments, a third guide bore may be positioned posterior of the first guide bore such that a second anterior-posterior distance is defined between the first guide bore and the third guide bore. The plurality of commonly-sized femoral trial components may include a third commonly-sized femoral trial component. A difference between the anterior-posterior distance of the first commonly-sized femoral trial component and the anterior-posterior distance of the third commonly-sized femoral trial component may be equal to the second anterior-posterior distance of the cutting block. The difference between the anterior-posterior distance of the first commonly-sized femoral trial component and the anterior-posterior distance of the third commonly-sized femoral trial component may be 1.5 millimeters. The second anterior-posterior distance of the cutting block may be 1.5 millimeters.

BRIEF DESCRIPTION OF THE DRAWINGS

The detailed description particularly refers to the following figures, in which.

DETAILED DESCRIPTION OF THE DRAWINGS

Figure 1:
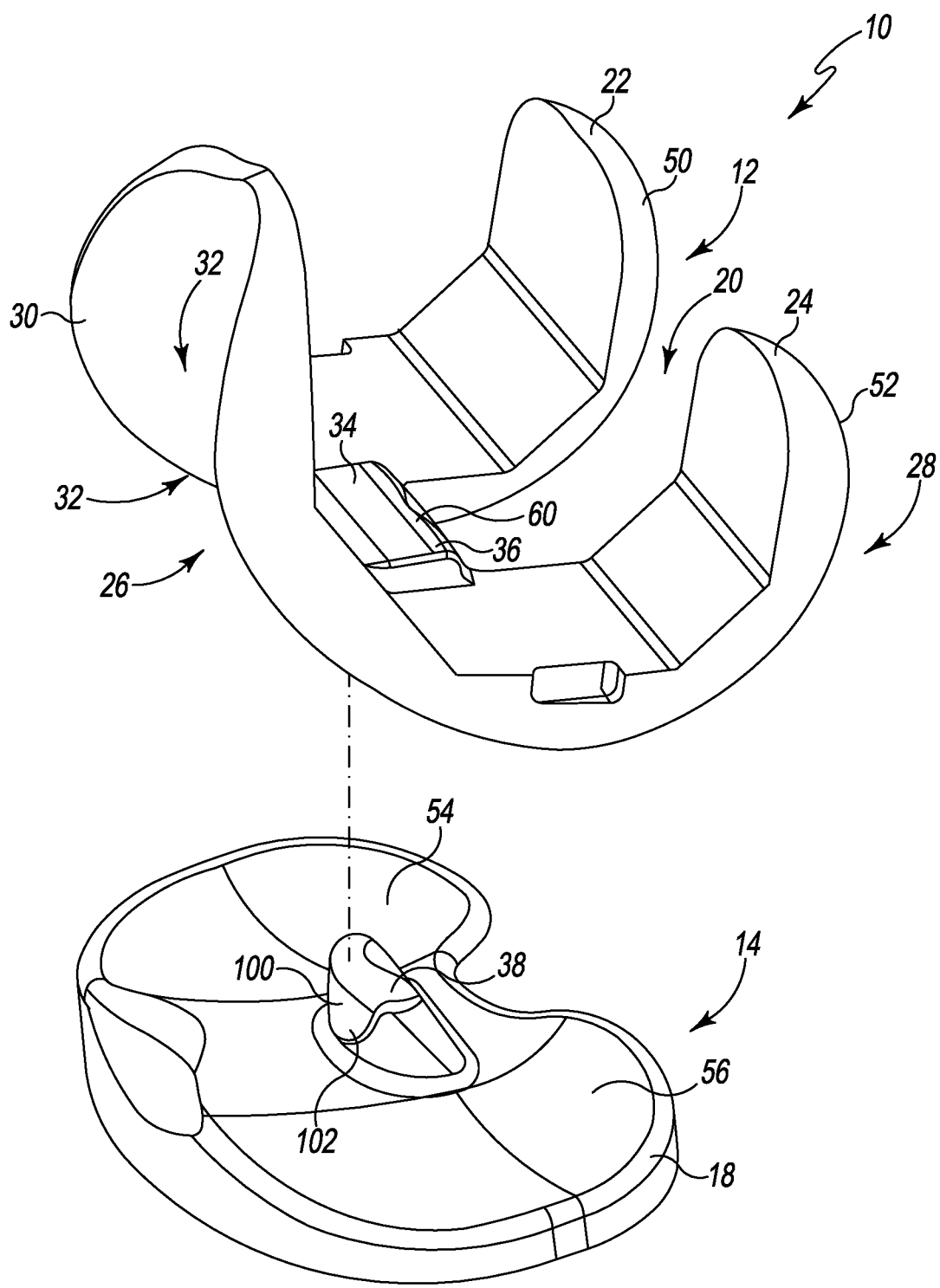
FIG. 1 is an exploded perspective view of an exemplary embodiment of a replacement knee prosthesis providing anterior stabilization.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an exemplary embodiment of an orthopedic knee implant 10 for use with total arthroplasty procedures is shown. The implant 10 includes a femoral component 12 and a tibial component 14 that is configured to permit the femoral component 12 to articulate over a range of flexion. In this exemplary embodiment, the tibial component 14 includes a tibial tray insert 18, which is configured to be attached to, for example, a tibial tray (not shown) secured to the proximal end of a patient's tibia. Such trays may include stems configured to be received within the intramedullary canal of the tibia. It should be appreciated that the tray may provide either a fixed bearing interface to lock the orientation of the tibial tray insert 18 with the tibial tray or a mobile bearing interface that allows the tibial tray insert 18 to move independent of the tibial tray. Additionally, in other embodiments, the tibial tray and the tibial tray insert may be combined into a single, monolithic component.

The femoral component 12 is illustratively formed from a metallic material such as cobalt-chromium or titanium, but may be formed from other materials, such as a ceramic material, a polymer material, a bio-engineered material, or the like, in other embodiments. The tibial tray insert 18 is illustratively formed from a polymer material such as an ultra-high molecular weight polyethylene (UHMWPE), but may be formed from other materials, such as a ceramic material, a metallic material, a bio-engineered material, or the like, in other embodiments.

As shown in FIG. 1, the femoral component 12 is illustratively a posterior cruciate retaining orthopedic femoral component that includes a posterior discontinuity or gap 20 between lateral and medial condyles 22, 24 to allow the femoral component to articulate between maximum extension and maximum flexion without impinging the posterior cruciate ligament (PCL), which is retained during the total arthroplasty procedure. In contrast, the anterior cruciate ligament (ACL) is sacrificed or removed during a total arthroplasty procedure. Those skilled in the art are familiar with the posterior constraint resulting from retention of the posterior cruciate ligament, whereas those skilled in the art are also familiar with the absence of anterior constraint resulting from the absence of the anterior cruciate ligament.

The exemplary femoral component 12 includes a pair of condyles 22, 24, each of which has an arcuate shape in order to allow for smooth articulation of the femur with respect to the tibia. In general, the femoral component includes an anterior portion 26 and a posterior portion 28. The anterior portion 26 includes a front exterior face 30 having a groove 32 adapted to receive at least a portion of a patella component. The femoral component 12 also includes an anterior cam 36, as described in greater detail below, is configured to engage a post 38 of the tibial component 14.

The implant 10 also includes a tibial tray insert 18. As described above, the tibial tray insert 18 includes bearing surfaces 54, 56 that are adapted to receive and engage the condyles 22, 24 of the femoral component 12. The two bearing surfaces 54, 56 are partially separated from one another by a post 38 upstanding from the tibial tray insert 18. In this exemplary embodiment, the post 38 is integrally formed with the tibial tray insert 18. However, it should be appreciated that the post 38 may be separable from the tibial tray insert 18 and its location is independent of the location/movement of the tibial tray insert.

The post 38 has an anterior surface or wall 100 that is configured to engage the posterior surface 60 of the cam 36 of the femoral component 12 when the implant 10 (and hence the knee) is at full extension and over part of flexion. The post 38 also includes a curved anterior section 102 that is sized to ensure the cam 36 disengages from the post 38. It should be appreciated that the post 38 may include other structure that is sized and shaped to ensure the cam 36 disengages from the post 38.

Figure 2:
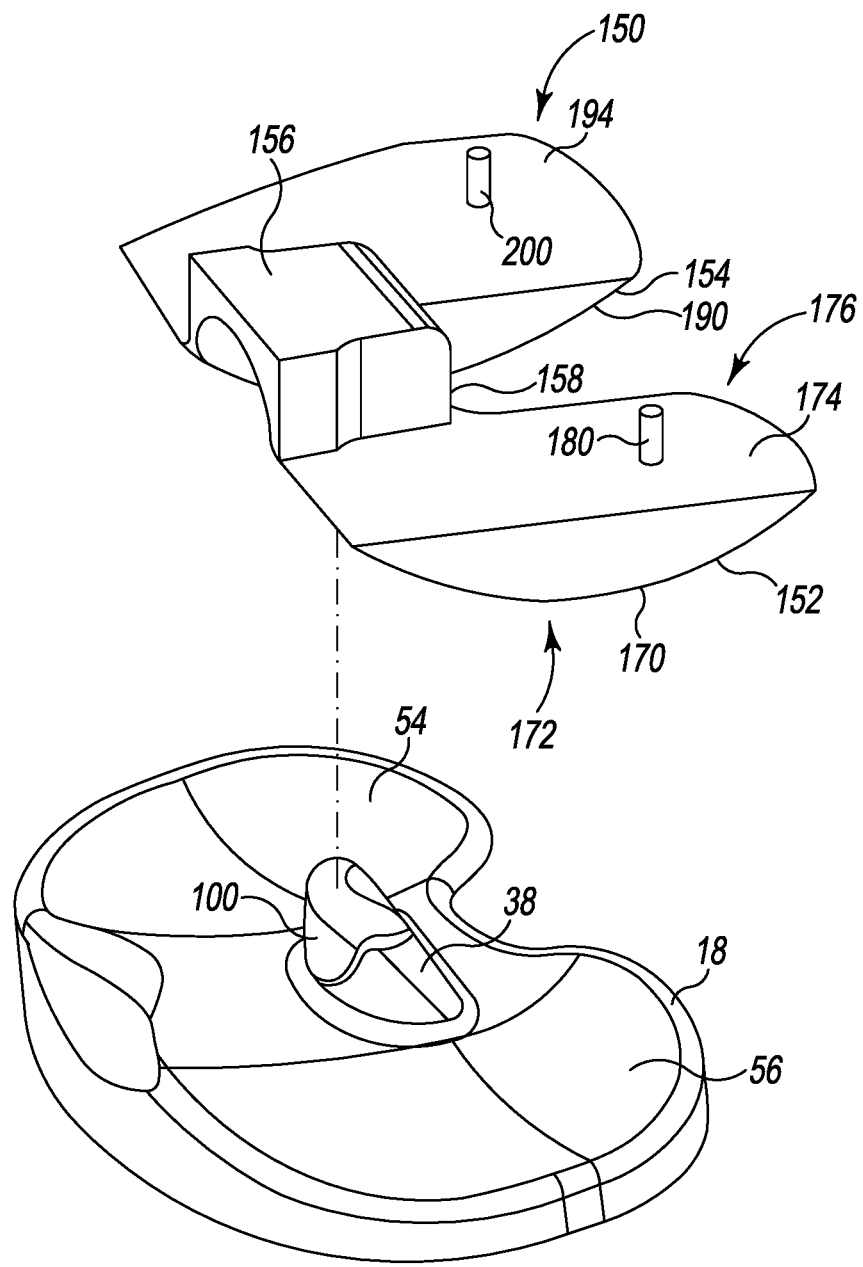
FIG. 2 is an exploded perspective view of an exemplary femoral trial component and tibial tray.

As illustrated in FIG. 2, a femoral trial component 150 is configured to articulate relative to the tibial tray insert 18 between full extension and full flexion to provide trialing for the femoral component 12. The femoral trial component 150 includes a medial femoral condyle 152 and a lateral femoral condyle 154. The medial femoral condyle 152 and the lateral femoral condyle 154 are joined by an anterior cam 156 having a posterior surface 158. The posterior surface 158 is configured to engage the anterior surface 100 of the post 38 when the femoral trial component 150 is positioned in full extension relative to the tibial tray insert 18. The posterior surface 158 is configured to disengage the anterior surface 100 of the post 38 when the femoral trial component 150 is positioned in full flexion relative to the tibial tray insert 18.

The medial femoral condyle 152 includes a medial articulation surface 170 on an inferior side 172 of the femoral trial component 150. The medial articulation surface 170 is configured to articulate relative to the bearing surface 56 of the tibial tray insert 18. A medial bone facing surface 174 extends along a superior side 176 of the femoral trial component 150 opposite the medial articulation surface 170. The medial bone facing surface 174 is configured to position against a resected end of a patient's femur. A medial peg 180 extends from the medial bone facing surface 174 in a superior direction.

The lateral femoral condyle 154 includes a lateral articulation surface 190 on the inferior side 172 of the femoral trial component 150. The lateral articulation surface 190 is configured to articulate relative to the bearing surface 54 of the tibial tray insert 18. A medial bone facing surface 194 extends along the superior side 176 of the femoral trial component opposite the lateral articulation surface 190. The lateral bone facing surface 194 is configured to position against the resected end of the patient's femur. A lateral peg 200 extends from the lateral bone facing surface 194 in a superior direction.

Figure 3:
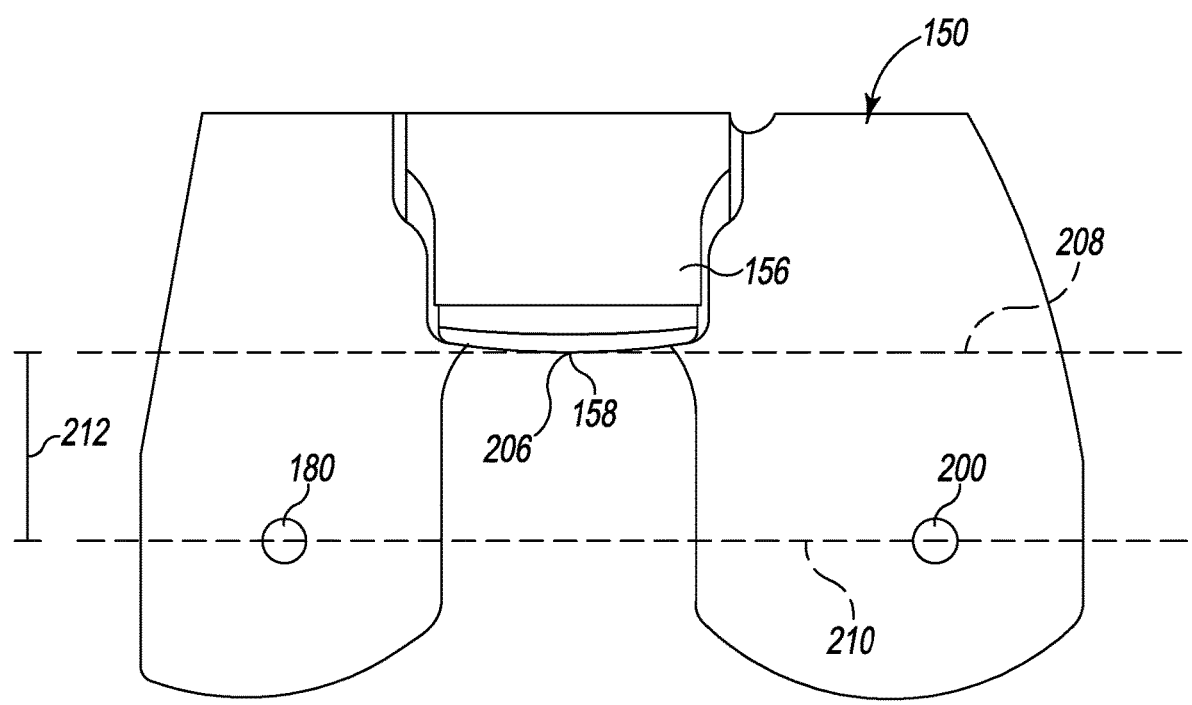
FIG. 3 is a top plan view of the femoral trial component of FIG. 2.

Referring to FIG. 3, an imaginary line 208 extends tangentially in a medial-lateral direction through the posterior-most point 206 of the posterior surface 158 of the anterior cam 156. The medial peg 180 and the lateral peg 200 are aligned along an imaginary line 210 that extends parallel to the imaginary line 208. The imaginary line 210 is positioned posteriorly of the posterior surface 158. As such, the medial peg 180 and the lateral peg 200 are positioned posteriorly from the posterior surface 158 of the anterior cam 156. The imaginary line 210 is positioned an anterior-posterior distance 212 from the imaginary line 208. Accordingly, the medial peg 180 and the lateral peg 200 are positioned the distance 212 from the imaginary line 208. That is, the medial peg 180 and the lateral peg 200 are positioned an equal distance from the posterior surface 158.

Figure 4:
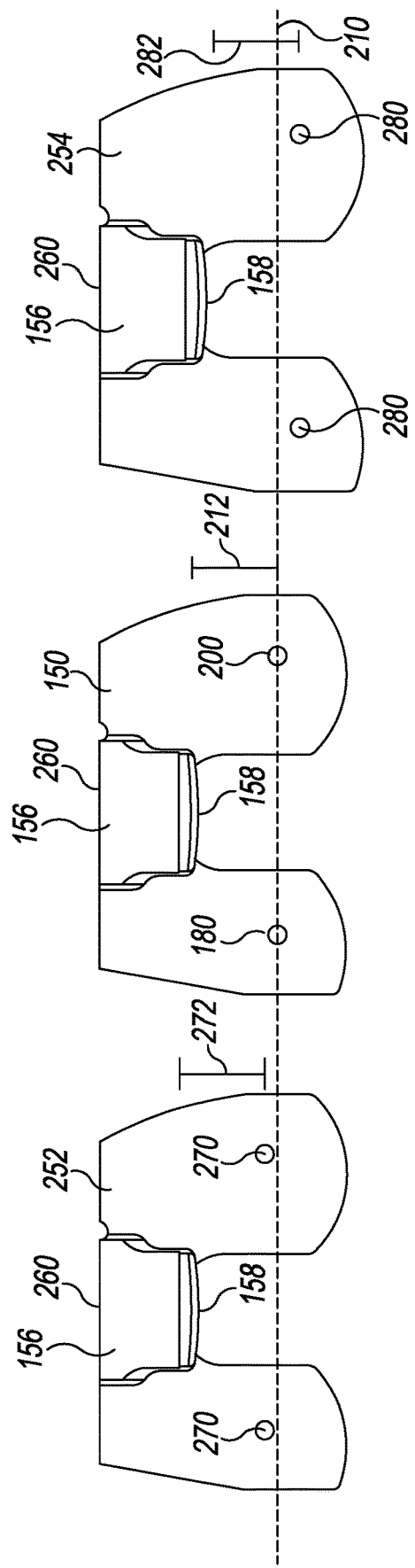
FIG. 4 is a top plan view of a plurality of femoral trial components having offset pegs.

Referring now to FIG. 4, a plurality of commonly-sized femoral trial components 250 includes the femoral trial component 150, a femoral trial component 252, and a femoral trial component 254. The femoral trial components are commonly-sized across a range of differently-sized femoral components 12. In the orientation of FIG. 4, each of the femoral trial components 150, 252, and 254 is aligned along their anterior ends 260. The imaginary line 210 extends across each component 150, 252, and 254. The imaginary line 210 extends through the medial peg 180 and lateral peg 200 of the femoral trial component 150. The medial peg 180 and the lateral peg 200 are positioned the distance 212 from the imaginary line 208.

The femoral trial component 252 includes pegs 270 that are offset from the imaginary line 210. The pegs 270 are positioned anteriorly from the imaginary line 210 so that the pegs are positioned an anterior-posterior distance 272 from the imaginary line 208. The distance 272 is less than the distance 212. In an exemplary embodiment, the distance 272 is 1.5 millimeters less than the distance 212. In other embodiments, the distance 272 may be between 0.5 millimeters and 3 millimeters less than the distance 212.

The femoral trial component 254 includes pegs 280 that are offset from the imaginary line 210. The pegs 280 are positioned posteriorly from the imaginary line 210 so that the pegs are positioned an anterior-posterior distance 282 from the imaginary line 208. The distance 282 is greater than the distance 212. In an exemplary embodiment, the distance 282 is 1.5 millimeters greater than the distance 212. In other embodiments, the distance 282 may be between 0.5 millimeters and 3 millimeters greater than the distance 212.

The femoral trial component 150 is configured to locate the patient's femur in a trialing position 300 (shown in FIG. 8) relative to the patient's tibia when the tibial component 14 is secured to a tibia of the patient. The femoral trial component 150 is also configured to locate the patient's femur in the trialing position 300 when the femoral trial component 150 is fixed relative to the patient's femur, and the femoral trial component 150 and the tibial component 18 are in the full extension position.

Figure 8:
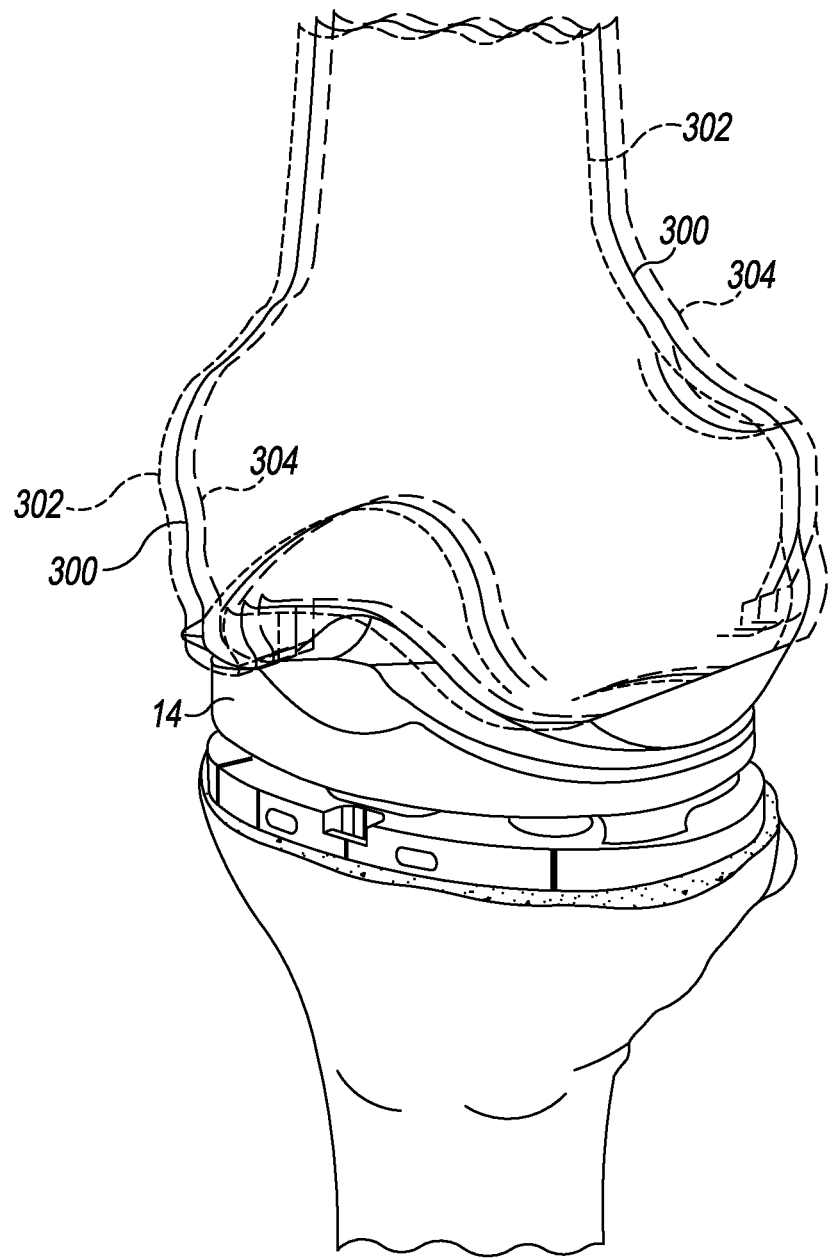
FIG. 8 is a side perspective view showing the various trialing positions produced by use of the plurality of femoral trial components of FIG. 4.
Figure 9:
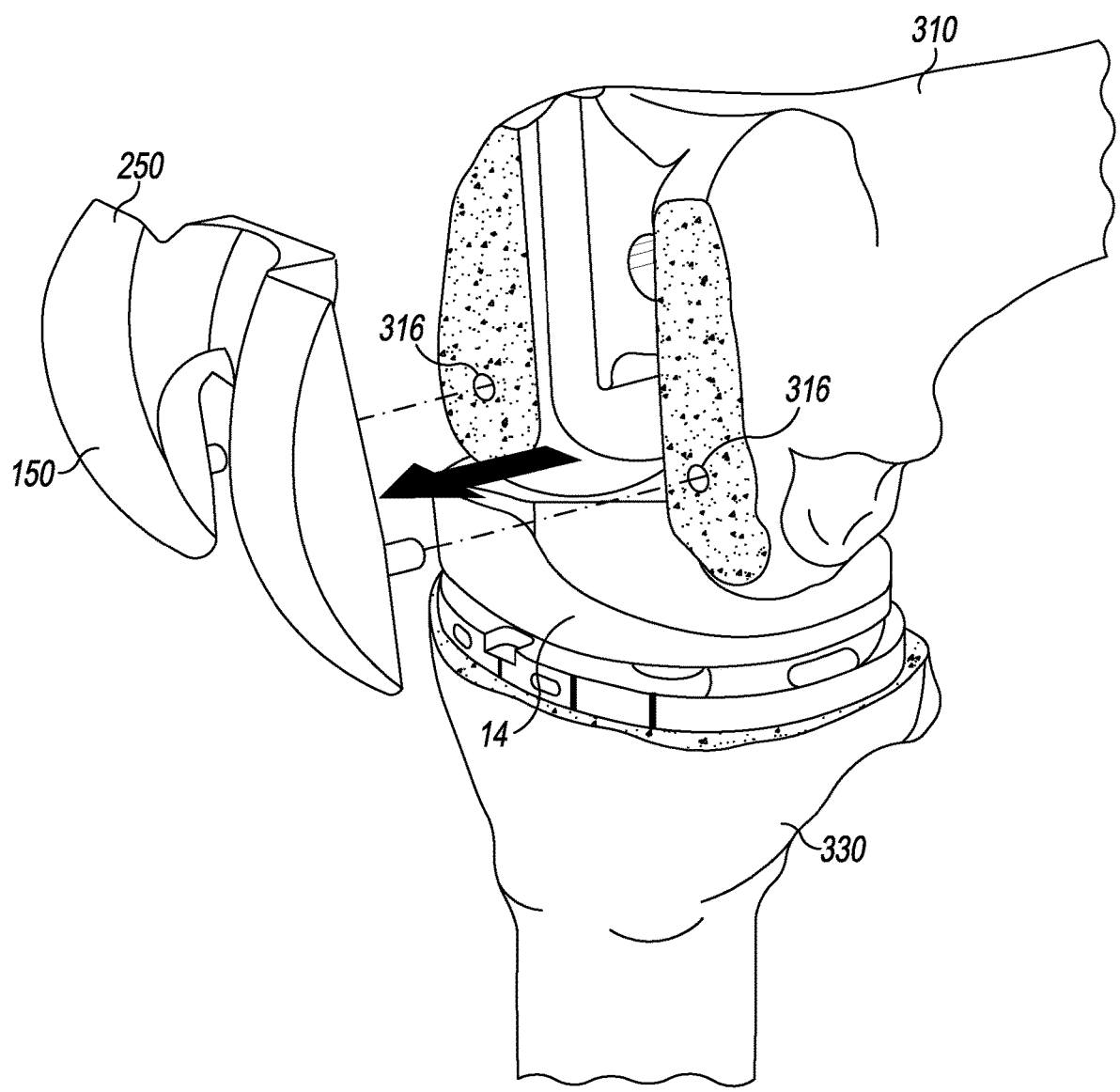
FIG. 9 is a side perspective view showing the femoral trial component being removed from the distal end of the femur.

The femoral trial component 252 is configured to locate the patient's femur in a trialing position 302 (shown in FIG. 8) relative to the patient's tibia when the tibial component 18 is secured to the patient's tibia. The femoral trial component 252 is also configured to locate the patient's femur in the trialing position 302 when the femoral trial component 252 is fixed relative to the patient's femur, and the femoral trial component 252 and the tibial component 18 are in the full extension position. As can be seen in FIG. 8, the trialing position 302 of the patient's femur is anterior of trialing position 300.

The femoral trial component 254 is configured to locate the patient's femur in a third trialing position 304 (shown in FIG. 8) relative to the patient's tibia when the tibial component 18 is secured to the patient's tibia. The femoral trial component 254 is also configured to locate the patient's femur in the trialing position 304 when the femoral trial component 254 is fixed relative to the patient's femur, and the femoral trial component 254 and the tibial component 18 are in the full extension position. As can be seen in FIG. 8, the trialing position 304 of the patient's femur is posterior of trialing position 300.

It should be noted that the plurality of commonly sized femoral trial components 250 may include any number of femoral trial components 250. The plurality of components 250 may include any number of components 250 having pegs that are positioned at various anterior distances from the imaginary line 210. The plurality of components 250 may also include any number of components 250 having pegs that are positioned at various posterior distances from the imaginary line 210.

Figure 5:
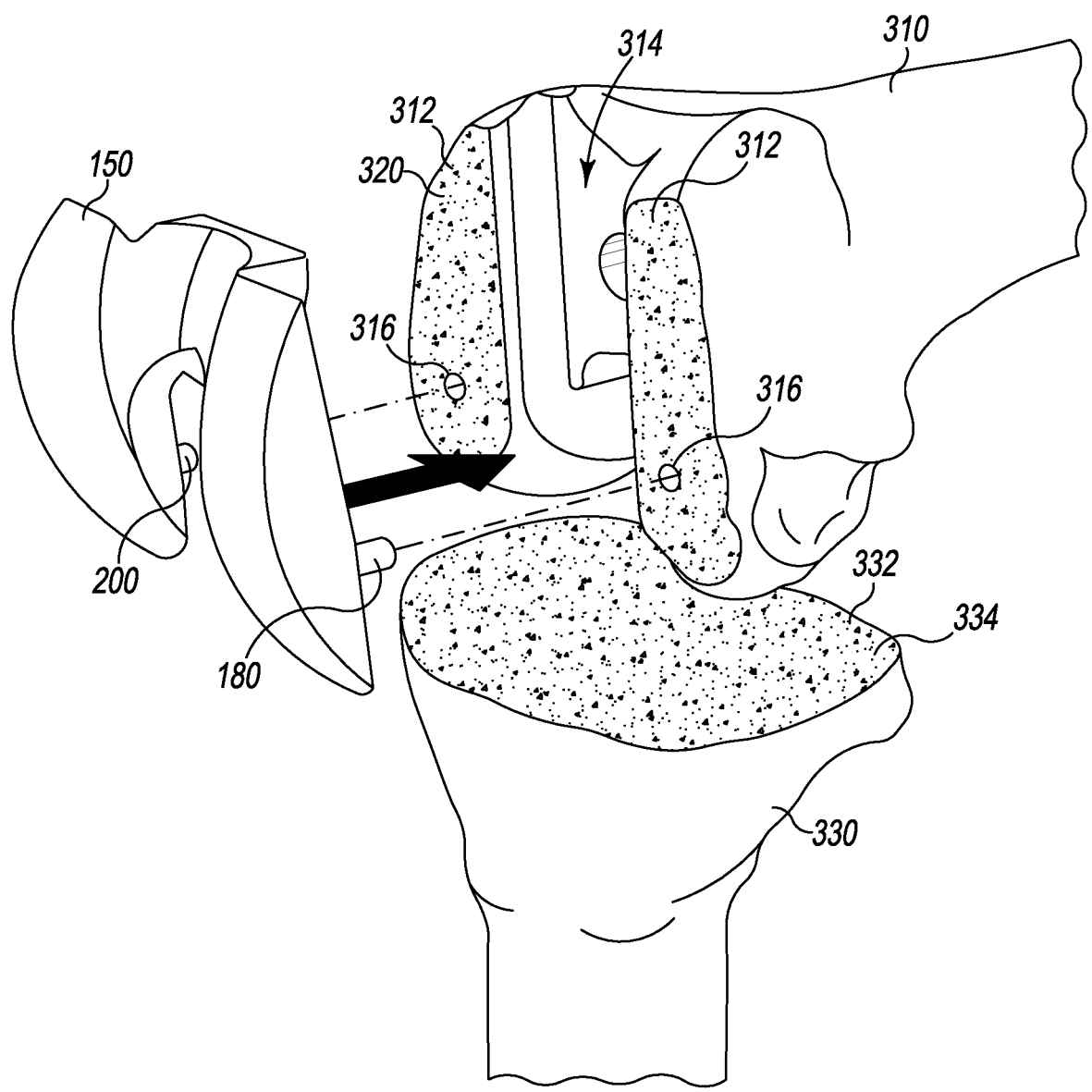
FIG. 5 is a side perspective view showing one of the femoral trial components of FIG. 4 being positioned on a distal end of a femur.

Referring now to FIG. 5, during an orthopaedic procedure, the patient's tibia 330 is resected to form a smooth surface 332 on a proximal end 334 of the tibia 330. Additionally, the patient's femur 310 is distally resected to form smooth condylar surfaces 312. A box cut 314 is formed between the condylar surfaces 312. Guide holes 316 are also formed in the surfaces 312. One example of a process for performing a distal resection and box cut, along with forming guide holes, is outlined in the Attune® Knee System: Intuition™ Instruments Surgical Technique (Revision 4), which is commercially available from DePuy Synthes and is expressly incorporated herein by reference.

Figure 6:
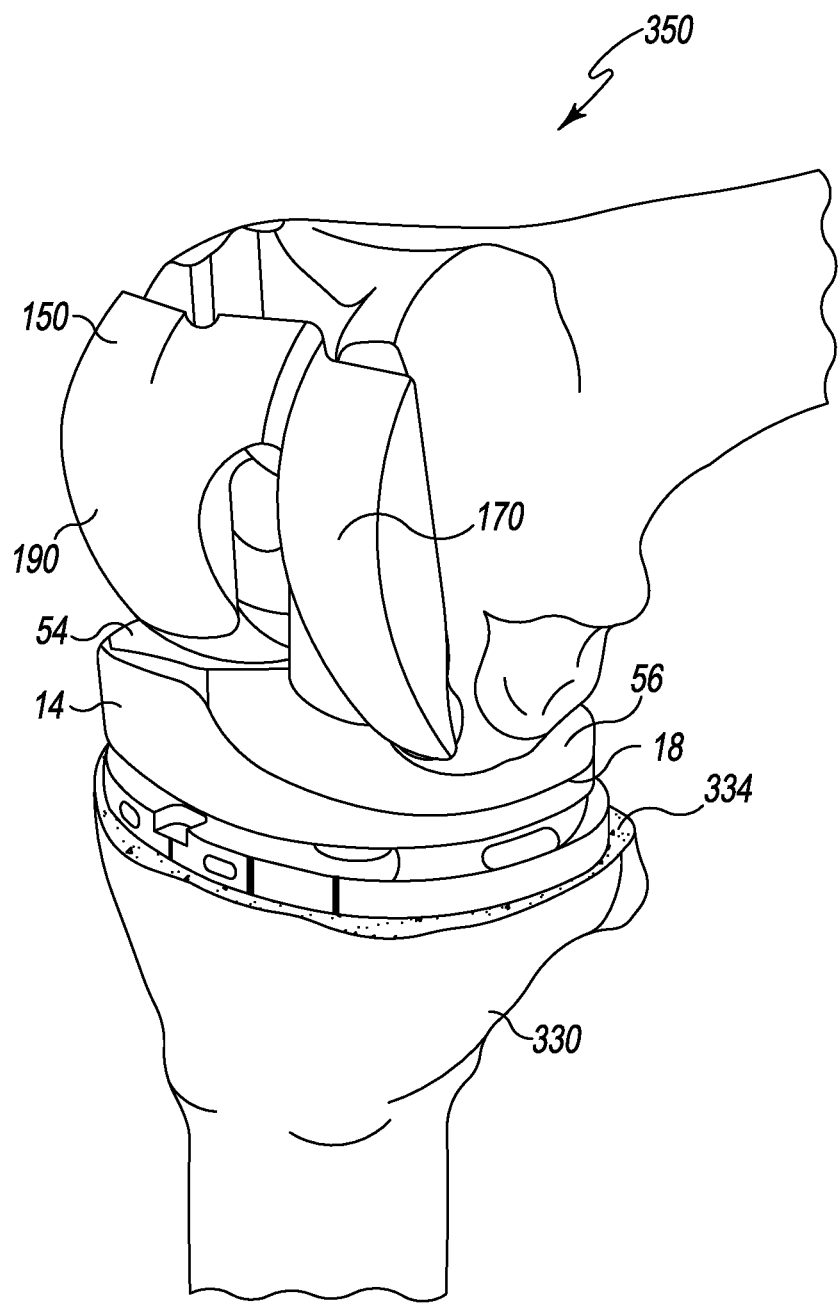
FIG. 6 is a side perspective view showing the femoral trial component positioned on the distal end of the femur and a tibial component positioned on the proximal end of a tibia with the femoral trial component and the tibial component positioned in full flexion.

A femoral trial component, for example femoral trial component 150 may be secured to the distal end 320 of the femur 310 as shown in FIG. 6. The femoral trial component 150 is secured such that the medial peg 180 and the lateral peg 200 are received in the guide holes 316. The femoral component 150 is engaged with the femur 310 so that the medial bone facing surface 174 and the lateral bone facing surface 194 contact the surfaces 312 of the femur.

Figure 7:
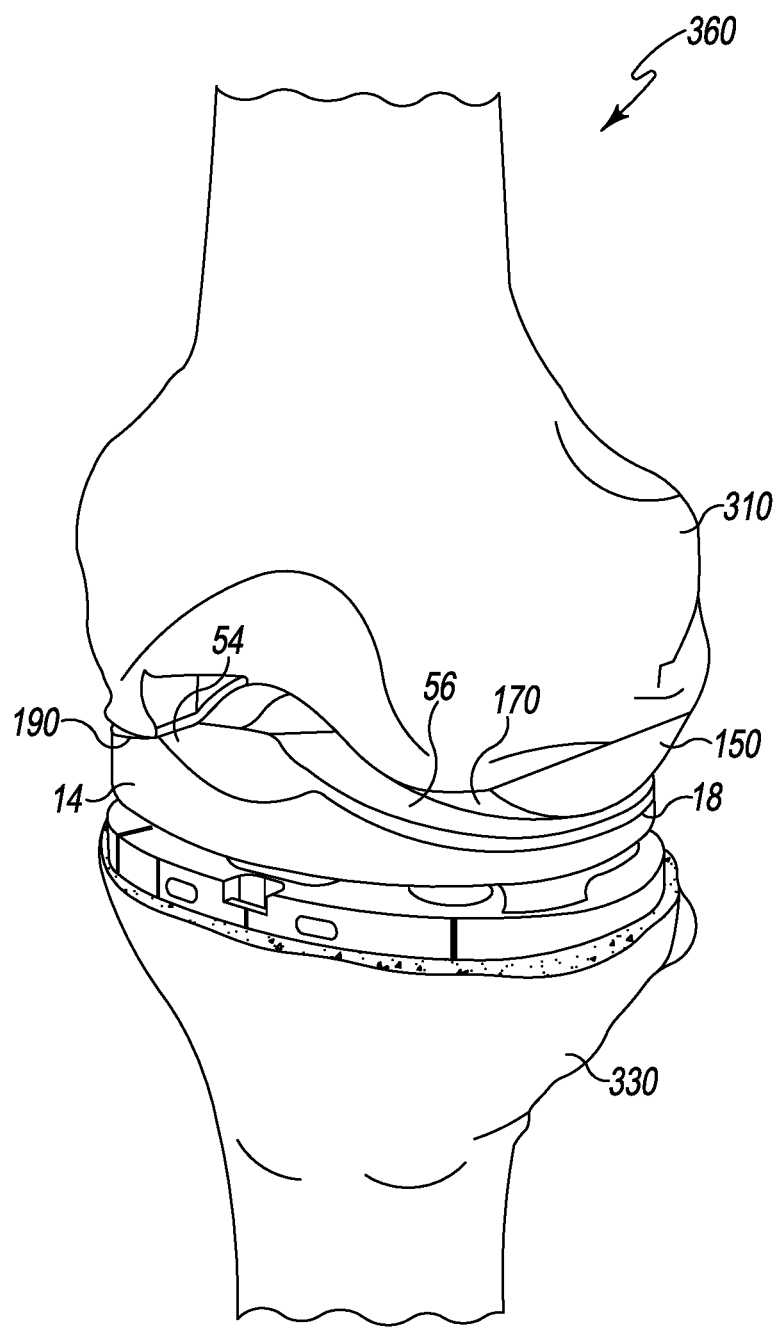
FIG. 7 is a view similar to FIG. 6, but showing the femoral trial component and the tibial component positioned in full extension.

A tibial component 14 having the tibial insert 18 is secured to the proximal end 334 of the tibia 330 and positioned against the surface 332. It should be appreciated that in other embodiments the tibial component may be a tibial trial component, which is attached to the proximal end 334 of the tibia 330. The femoral trial component 150 is then trialed by the surgeon by moving the component 150 relative to the tibial insert 18 between full flexion 350 (shown in FIG. 6) and full extension 360 (shown in FIG. 7). As illustrated in FIG. 8, the surgeon may trial with each of the plurality of femoral components 250 to determine which component provides a desired contact point between the medial articulation surface 170, the lateral articulation surface 190 and the bearing surfaces 54, 56.

Figure 10:
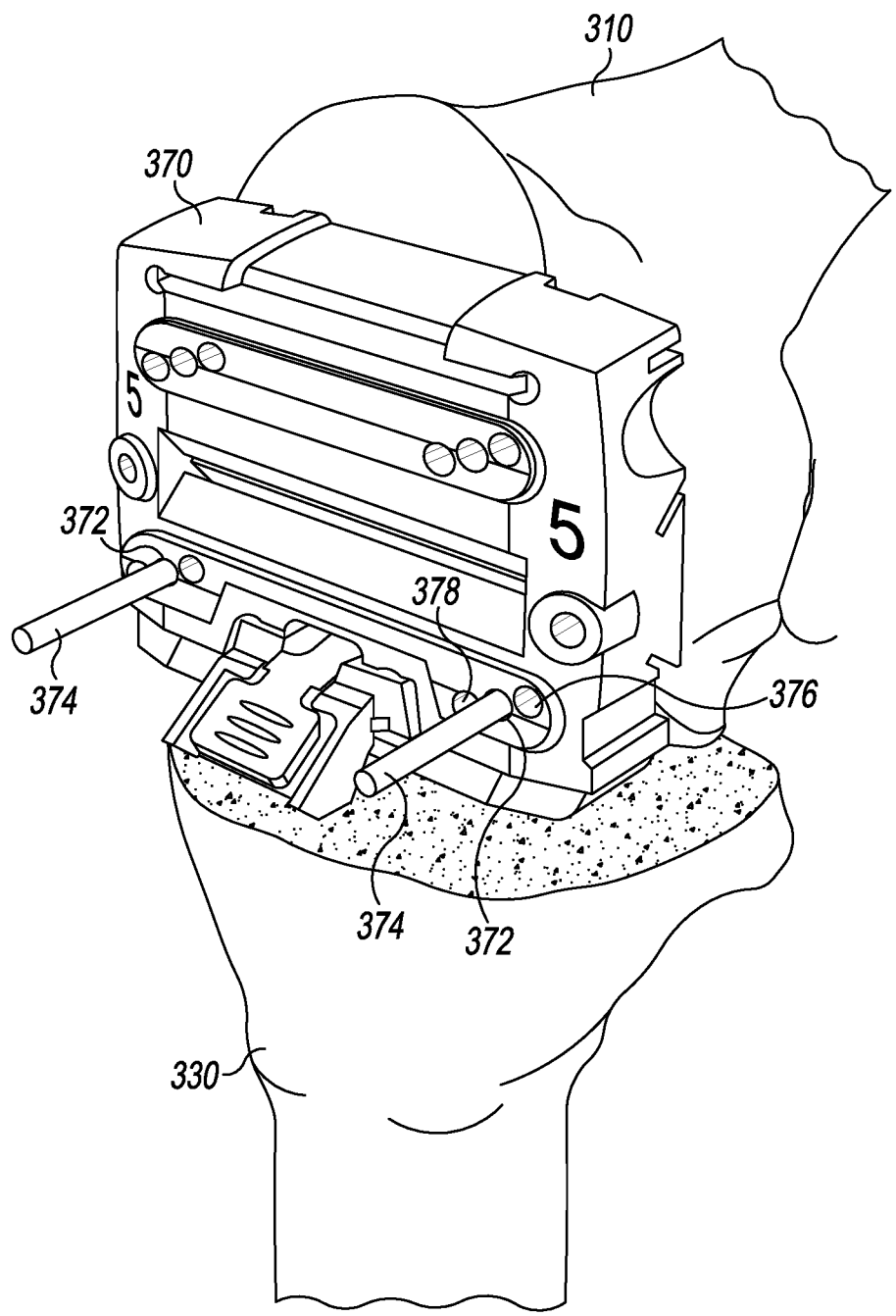
FIG. 10 is a side perspective view showing a cutting block positioned on the distal end of the femur.

After trialing with one or more of the components 250, the surgeon selects a cutting block position based on the femoral trial component that provided the desired articulation. Referring to FIG. 10, a cutting block 370 is then secured to the end 312 of the femur 310 to complete additional resections on the femur 310 via pins 374 that are inserted though the pin holes 372, 374, or 378 and the guide holes 316 to secure the cutting block 370 to the femur 310. Accordingly, the guide holes 316 are utilized to secure both the femoral trial components 250 and the cutting block 370.

The cutting block 370 includes pin holes 372, 376, 378 that align with the guide holes 316 to position the cutting block in the desired position. Each set of pin holes 372, 374, 378 are spaced apart by an anterior-posterior distance that corresponds to positioning of the pegs of each femoral trial component. For example, if the surgeon selects femoral trial component 150, the surgeon positions the cutting block 370 using pin holes 372. If, on the other hand, the surgeon selects the femoral trial component 252, the surgeon positions the cutting block 370 using pin holes 376. An anterior-posterior distance between the pin holes 376 and the pin holes 372 corresponds to an anterior-posterior distance between the pegs 270 of the femoral trial component 252 and the pegs 180, 200 of the femoral trial component 150. If the surgeon selects the femoral trial component 254, the surgeon positions the cutting block 370 using pin holes 378. An anterior-posterior distance between the pin holes 378 and the pin holes 372 corresponds to an anterior-posterior distance between the pegs 280 of the femoral trial component 254 and the pegs 180, 200 of the femoral trial component 150. As such, the cutting block 270 is positioned on the femur 310 in an orientation that corresponds to the selected femoral trial component 250 by aligning the appropriate pin holes 372, 376, and 378 with the guide holes 316.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical system for a total knee implant, the system comprising:
    a plurality of commonly-sized femoral trial components, each commonly-sized femoral trial component including:
        a first femoral condyle having a first articulation surface configured to engage a tibial component and a first bone-facing surface positioned opposite the first articulation surface and configured to engage a distal end of a patient's femur,
        a second femoral condyle spaced apart from the first femoral condyle, the second femoral condyle having a second articulation surface configured to engage the tibial component, and a second bone-facing surface positioned opposite the second articulation surface and configured to engage the distal end of the patient's femur,
        an anterior cam positioned between the first femoral condyle and the second femoral condyle, the anterior cam configured to engage an anterior surface of the tibial component, and
        a peg extending away from the first bone-facing surface,
    wherein: (i) an anterior-posterior distance is defined between the peg and the anterior cam, and (ii) each commonly-sized femoral trial component of the plurality of commonly-sized femoral trial components has an anterior-posterior distance that is different than the anterior-posterior distance of every other commonly-sized femoral trial component included in the plurality of commonly-sized femoral trial components, the orthopaedic surgical system further comprising a cutting block including (i) a bone-engaging surface, (ii) an outer surface positioned opposite the bone-engaging surface, and (iii) a pair of guide bores including a first and second guide bore each extending through the bone-engaging surface and the outer surface of the cutting block, wherein an anterior-posterior distance of the first and second guide bores corresponds to the anterior-posterior distance of one of the plurality of femoral trial components.

2. The orthopaedic surgical system of claim 1, wherein:
the anterior cam includes a posterior surface configured to engage the anterior surface of the tibial component, and
the peg is positioned posteriorly of the anterior cam.

3. The orthopaedic surgical system of claim 1, wherein:
each commonly-sized femoral trial component of the plurality of commonly-sized femoral trial components further includes a second peg extending away from the second bone-facing surface, and
the first and second pegs are positioned an equal distance away from the anterior cam in the anterior-posterior direction.

4. The orthopaedic surgical system of claim 1, wherein:
the plurality of commonly-sized femoral trial components includes a first femoral trial component and a second femoral trial component, and
the second femoral trial component has an anterior-posterior distance that is about 1.5 millimeters less than the anterior-posterior distance of the first femoral trial component.

5. The orthopaedic surgical system of claim 4, wherein the plurality of commonly-sized femoral trial components includes a third femoral trial component having an anterior-posterior distance that is about 1.5 millimeters greater than the anterior-posterior distance of the first femoral trial component.

6. An orthopaedic surgical system comprising:
a tibial component including a first bearing surface, a second bearing surface spaced apart from the first bearing surface, and a post positioned between the first and second bearing surfaces, and
a plurality of commonly-sized femoral trial components configured to articulate relative to the tibial component between a full extension position and a full flexion position, each commonly-sized femoral trial component of the plurality of commonly-sized femoral trial components including: (i) a first femoral condyle having a first articulation surface sized and shaped to articulate on the first bearing surface of the tibial component and a first bone-facing surface positioned opposite the first articulation surface and configured to engage a distal end of a patient's femur, (ii) a second femoral condyle spaced apart from the first femoral condyle, the second femoral condyle having a second articulation surface sized and shaped to articulate on the second bearing surface of the tibial component and a second bone-facing surface positioned opposite the second articulation surface and configured to engage the distal end of the patient's femur, (iii) an anterior cam positioned between the first femoral condyle and the second femoral condyle, the anterior cam having a posterior surface configured to engage an anterior surface of the post of the tibial component, and (iv) a peg positioned posteriorly of the anterior cam, extending away from the first bone-facing surface, and configured to engage the distal end of the patient's femur to fix the femoral trial component relative to the patient's femur, wherein: (i) an anterior-posterior distance is defined between the peg and the anterior cam, and (ii) each commonly-sized femoral trial component of the plurality of commonly-sized femoral trial components has an anterior-posterior distance that is different than the anterior-posterior distance of every other commonly-sized femoral trial component included in the plurality of commonly-sized femoral trial components, the orthopaedic surgical system further comprising a cutting block including (i) a bone-engaging surface, (ii) an outer surface positioned opposite the bone-engaging surface, and (iii) a pair of guide bores including a first and second guide bore each extending through the bone-engaging surface and the outer surface of the cutting block, wherein an anterior-posterior distance of the first and second guide bores corresponds to the anterior-posterior distance of one of the plurality of femoral trial components.

7. The orthopaedic surgical system of claim 6, wherein the posterior surface of the anterior cam of each commonly-sized femoral trial component is engaged with the anterior surface of the post when the femoral trial component and the tibial component are in the full extension position.

8. The orthopaedic surgical system of claim 7, wherein:
the plurality of femoral trial components includes a first femoral trial component having an anterior-posterior distance,
the first femoral trial component is configured to locate the patient's femur in a first trialing position relative to the patient's tibia when (i) the tibial component is secured to a tibia of the patient, (ii) the first femoral trial component is fixed relative to the patient's femur, and (iii) the first femoral trial component and the tibial component are in the full extension position,
the plurality of femoral trial components includes a second femoral trial component having an anterior-posterior distance that is less than the anterior-posterior distance of the first femoral trial component,
the second femoral trial component is configured to locate the patient's femur in a second trialing position relative to the patient's tibia when (i) the tibial component is secured to the patient's tibia, (ii) the second femoral trial component is fixed relative to the patient's femur, and (iii) the second femoral trial component and the tibial component are in the full extension position, and
the second trialing position of the patient's femur is anterior of the first trialing position.

9. The orthopaedic surgical system of claim 8, wherein:
the plurality of femoral trial components includes a third femoral trial component having an anterior-posterior distance that is greater than the anterior-posterior distance of the first femoral trial component,
the third femoral trial component is configured to locate the patient's femur in a third trialing position relative to the patient's tibia when (i) the tibial component is secured to the patient's tibia, (ii) the third femoral trial component is fixed relative to the patient's femur, and (iii) the third femoral trial component and the tibial component are in the full extension position, and
the third trialing position of the patient's femur is posterior of the first trialing position.

10. The orthopaedic surgical system of claim 6, wherein the posterior surface of the anterior cam of each commonly-sized femoral trial component disengages from the anterior surface of the post as the femoral trial component articulates relative to the tibial component toward the full flexion position.

11. The orthopaedic surgical system of claim 6, wherein:
each commonly-sized femoral trial component further includes a second peg extending away from the second bone facing surface, and
the first and second pegs are spaced apart a first medial-lateral distance and positioned an equal distance away from the anterior cam in the anterior-posterior direction.

12. The orthopaedic surgical system of claim 11, wherein the first and second guide bores are spaced apart a second medial-lateral distance equal to the first medial-lateral distance.

13. The orthopaedic surgical system of claim 12, wherein the cutting block includes a plurality of pairs of guide bores extending through the bone-engaging surface and the outer surface of the cutting block, and
each pair of guide bores includes a first and second guide bore spaced apart the second medial-lateral distance.

14. A method of using an orthopaedic surgical system comprising:
securing a tibial component to a proximal end of a patient's tibia,
selecting a first femoral trial component including: (i) a first femoral condyle, (ii) a second femoral condyle spaced apart from the first femoral condyle, (iii) an anterior cam positioned between the first femoral condyle and the second femoral condyle, (iv) a first peg extending from the first femoral condyle, positioned posteriorly of the anterior cam, and spaced apart a first anterior-posterior distance from the anterior cam, and (v) a second peg extending from the second femoral condyle, positioned posteriorly of the anterior cam, and spaced apart the first anterior-posterior distance from the anterior cam,
inserting the first and second pegs of the first femoral trial component into a pair of surgically prepared holes formed in a distal end of the patient's femur to fix the first femoral trial component relative to the patient's femur,
removing the first femoral trial component from the patient's femur,
selecting a second femoral trial component including: (i) a first femoral condyle, (ii) a second femoral condyle spaced apart from the first femoral condyle, (iii) an anterior cam positioned between the first femoral condyle and the second femoral condyle, (iv) a first peg extending from the first condyle, positioned posteriorly of the anterior cam, and spaced apart a second anterior-posterior distance from the anterior cam, and (v) a second peg extending from the second femoral condyle, positioned posterior of the anterior cam, and spaced apart the second anterior-posterior distance from the anterior cam, wherein the second anterior-posterior distance is less than the first anterior-posterior distance,
inserting the first and second pegs of the second femoral trial component into the pair of surgically prepared holes formed in the distal end of the patient's femur to fix the second femoral trial component relative to the patient's femur,
aligning a pair of guide bores of a femoral cutting block with a pair of fixation pins inserted into the surgically prepared holes formed in the distal end of the patient's femur, the femoral cutting block having a bone-engaging surface and an outer surface positioned opposite the bone-engaging surface, and wherein the pair of guide bores extend through the bone-engaging surface and the outer surface of the femoral cutting block, and
advancing the femoral cutting block into engagement with the distal end of the patient's femur by advancing the guide bores of the femoral cutting block along the fixation pins.

15. The method of claim 14, further comprising:
selecting a third femoral trial component including: (i) a first femoral condyle, (ii) a second femoral condyle spaced apart from the first femoral condyle, (iii) an anterior cam positioned between the first femoral condyle and the second femoral condyle, (iv) a first peg extending from the first femoral condyle, positioned posterior of the anterior cam, and spaced apart a third anterior-posterior distance from the anterior cam, and (iv) a second peg extending from the second femoral condyle, positioned posteriorly of the anterior cam, and spaced apart the third anterior-posterior distance from the anterior cam, wherein the third anterior-posterior distance is greater than the first anterior posterior distance, and
inserting the first and second pegs of the third femoral trial component into the pair of surgically prepared holes formed in the distal end of the patient's femur to fix the third femoral trial component relative to the patient's femur.

16. The method of claim 15, further comprising:
articulating the first femoral trial component relative to the tibial component into a full extension position to move the patient's femur into a first position relative to the patient's tibia, and
articulating the second femoral trial component relative to the tibial component into the full extension position to move the patient's femur into a second position relative to the patient's tibia,
wherein the second position is located anterior of the first position.

17. The method of claim 16, further comprising:
rotating the third femoral trial component relative to the tibial component into the full extension position to move the patient's femur into a third position relative to the patient's tibia,
wherein the third position is located posterior of the first position.

18. The method of claim 17, further comprising selecting the cutting block having first and second guide bores including an anterior-posterior distance that corresponds to the anterior-posterior distance of one of the plurality of femoral trial components.

* * * * *